(12) United States Patent
Shi et al.

(10) Patent No.: US 11,701,077 B2
(45) Date of Patent: Jul. 18, 2023

(54) CODED-MASK-BASED X-RAY PHASE-CONTRAST AND DARK-FIELD IMAGING

(71) Applicant: UCHICAGO ARGONNE, LLC, Chicago, IL (US)

(72) Inventors: Xianbo Shi, Naperville, IL (US); Zhi Qiao, Darien, IL (US); Michael J. Wojcik, Orland Park, IL (US); Lahsen Assoufid, Chicago, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 101 days.

(21) Appl. No.: 17/185,387

(22) Filed: Feb. 25, 2021

(65) Prior Publication Data
US 2022/0265231 A1    Aug. 25, 2022

(51) Int. Cl.
*A61B 6/00*    (2006.01)
*A61B 6/06*    (2006.01)
(Continued)

(52) U.S. Cl.
CPC ............. *G01T 1/295* (2013.01); *A61B 6/40* (2013.01); *A61B 6/4035* (2013.01);
(Continued)

(58) Field of Classification Search
CPC ....... A61B 6/032; A61B 6/035; A61B 6/4035; A61B 6/4291; A61B 6/484; A61B 6/52;
(Continued)

(56) References Cited

U.S. PATENT DOCUMENTS

| 4,209,780 A | * | 6/1980 | Fenimore | ................ G01T 1/295 |
| | | | | 382/324 |
| 4,566,112 A | * | 1/1986 | Linde | ..................... A61B 6/025 |
| | | | | 378/23 |

(Continued)

FOREIGN PATENT DOCUMENTS

EP    1123491 A1    8/2001

OTHER PUBLICATIONS

Zhi Qiao et al., High-Resolution Scanning Coded-Mask-Based X-ray Multi-Contrast Imaging and Tomography, Journal of Imaging 2021, 7, 249. (Year: 2021).*

(Continued)

*Primary Examiner* — Allen C. Ho
(74) *Attorney, Agent, or Firm* — Marshall, Gerstein & Borun LLP

(57) ABSTRACT

Phase contrast and dark-field X-ray imaging enable imaging of objects that absorb or reflect very little X-ray light. Disclosed is a method and systems for performing coded-mask-based multi-contrast imaging (CMMI). The method includes providing radiation to a coded mask that has a known phase and absorption profile according to a pre-determined pattern. The radiation is then impingent upon a sample, and the radiation is detected to perform phase-reconstruction and image processing. The method and associated systems allow for the use of maximum-likelihood and machine learning methods for reconstruction images of the sample from the detected radiation.

20 Claims, 9 Drawing Sheets

(51) Int. Cl.
*G01N 23/04* (2018.01)
*G01N 23/041* (2018.01)
*G01T 1/29* (2006.01)
*G21K 1/02* (2006.01)

(52) U.S. Cl.
CPC .......... *A61B 6/4085* (2013.01); *A61B 6/4291* (2013.01); *A61B 6/484* (2013.01); *A61B 6/584* (2013.01); *G01N 23/04* (2013.01); *G01N 23/041* (2018.02); *G21K 1/02* (2013.01); *G21K 1/025* (2013.01)

(58) Field of Classification Search
CPC ... A61B 6/5205; A61B 6/5211; A61B 6/4085; G21K 1/02; G21K 1/025; G01N 23/041
USPC ............................... 378/2, 62, 145, 147, 149
See application file for complete search history.

(56) References Cited

U.S. PATENT DOCUMENTS

| | | | | |
|---|---|---|---|---|
| 4,677,681 A * | 6/1987 | Klausz | .................... | G21K 1/025 378/98.12 |
| 5,606,165 A * | 2/1997 | Chiou | .................... | G01T 1/295 382/281 |
| 5,717,733 A * | 2/1998 | Kurbatov | ............. | G01N 23/207 378/71 |
| 5,930,314 A * | 7/1999 | Lanza | .................... | G01N 23/22 250/363.06 |
| 6,737,652 B2 * | 5/2004 | Lanza | .................... | G01T 1/295 250/237 R |
| 7,463,712 B2 * | 12/2008 | Zhu | ........................ | A61B 6/583 378/7 |
| 7,623,614 B2 * | 11/2009 | Shefsky | .................. | G01T 1/295 378/87 |
| 7,693,256 B2 * | 4/2010 | Brahme | ................. | A61B 6/022 378/62 |
| 8,194,821 B2 * | 6/2012 | Seppi | ....................... | G21K 1/10 378/62 |
| 9,952,163 B2 * | 4/2018 | Endrizzi | ................ | A61B 6/484 |
| 10,993,686 B2 * | 5/2021 | Nebosis | ................ | H04N 25/63 |
| 11,073,427 B2 * | 7/2021 | Wang | .................... | G01J 9/0215 |
| 11,154,264 B2 * | 10/2021 | Yaroshenko | ......... | A61B 6/4291 |
| 2019/0265107 A1 | 8/2019 | Wang et al. | | |

OTHER PUBLICATIONS

Zhi Qiao et al., Single-shot x-ray phase-contrast and dark-field imaging based on coded binary phase mask, Applied Physics Letters 119, 011105 (2021). (Year: 2021).*
E. E. Fenimore and T. M. Cannon, Uniformly redundant arrays: digital reconstruction methods, Applied Optics 20(10), 1858-1864 (1981). (Year: 1981).*
E. E. Fenimore, Coded aperture imaging: the modulation transfer function for uniformly redundant arrays. Applied Optics 19(14), 2465-2471 (1980). (Year: 1980).*
T. M. Cannon and E. E. Fenimore, Tomographic imaging using uniformly redundant arrays, Applied Optics 18(7), 1052-1057(1979). (Year: 1979).*
E. E. Fenimore, Coded aperture imaging: predicted performance of uniformly redundant arrays, Applied Optics 17(22), 3562-3570 (1978). (Year: 1978).*
E. E. Fenimore and T. M. Cannon, Coded aperture imaging with uniformly redundant arrays, Applied Optics 17(3), 337-347 (1978). (Year: 1978).*
Bech, M., Tapfer, A., Velroyen, A. et al. In-vivo dark-field and phase-contrast x-ray imaging. *Sci Rep* 3, 3209 (2013). https://doi.org/10.1038/srep03209.
Wang, H et al. Sci. Rep. 6, 20476 (2016).
Wang, H et al. Sci. Rep. 5, 8762 (2015).
W. Grizolli, X. Shi, L. Assoufid, T. Kolodziej, and Y. Shvyd'ko, Proc. SPIE, 10385, 1038502 (2017).
Yogesh Kashyap, et al, Opt. Express 24, 18664-18673 (2016).
Bruker Corporation: SkyScan 1294 Brochure, "Phase Contrast Desk-Top X-Ray Microtomograph" @ 2015 Bruker microCT.
Grating-Interferometry Breast-Computed-Tomography (GI-BCT) system, retrieved on Jan. 24, 2023 GratXray: <https://www.gratxray.com>.
KA Image: incite microCT system retrieved on Jan. 24, 2023: https://web.archive.org/web/20221201123929/https://www.kaimaging.com/science-center/incite-technology/.

* cited by examiner

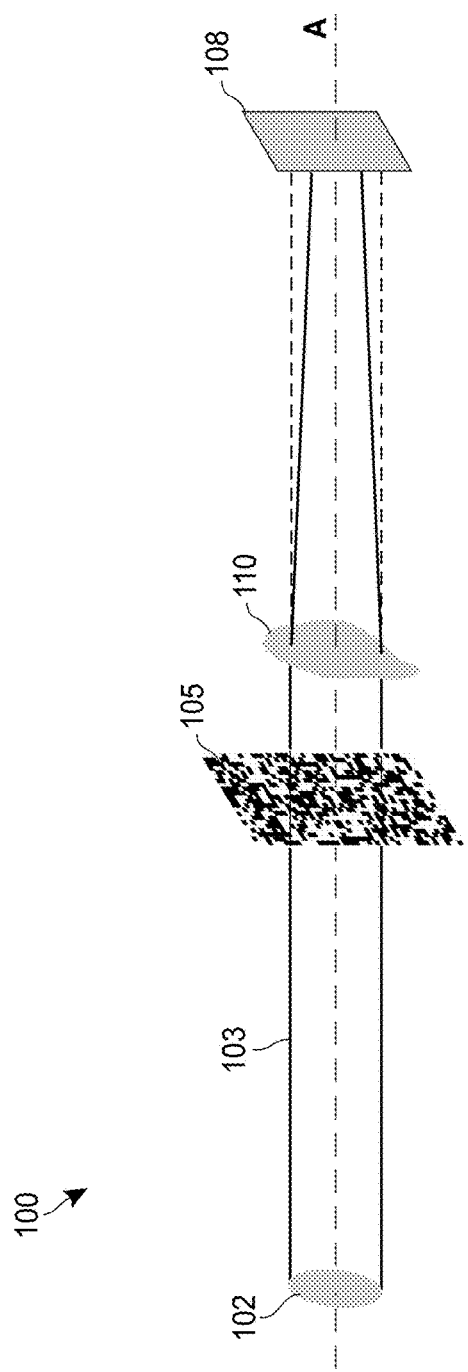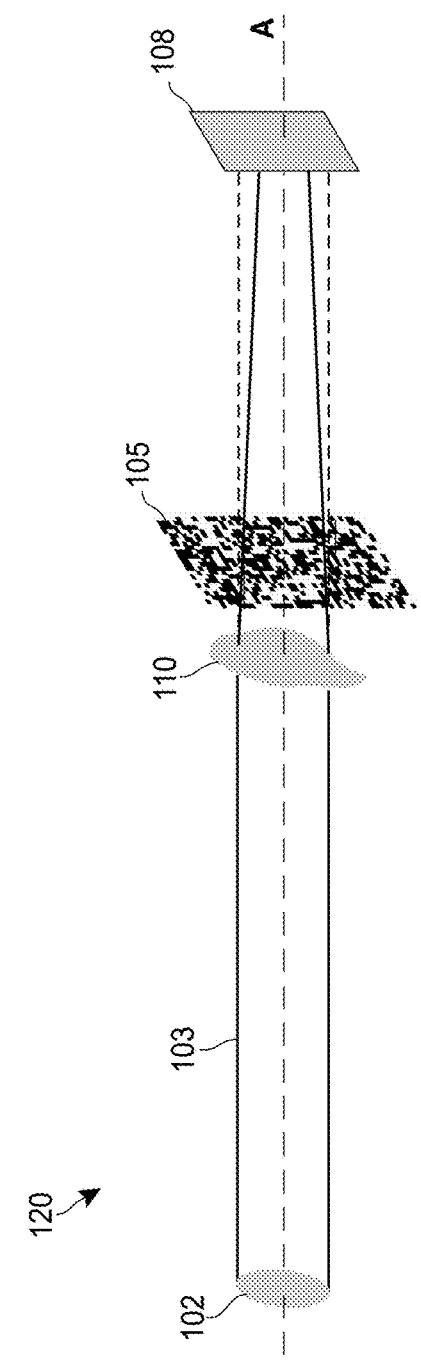

CODED-MASK-BASED X-RAY PHASE-CONTRAST AND DARK-FIELD IMAGING

This invention was made with government support under Contract No. DE-AC02-06CH11357 awarded by the United States Department of Energy to UChicago Argonne, LLC, operator of Argonne National Laboratory. The government has certain rights in the invention.

FIELD OF THE DISCLOSURE

The present disclosure relates to methods and systems for performing X-ray imaging, and specifically to phase contrast and dark-field imaging techniques.

BACKGROUND

X-ray imaging techniques are widely used in medical systems for diagnosing patients with a variety of conditions including bone fractures, tumors, dental issues, digestive problems, heart problems, and more. Recently, X-ray imaging has gained interest in other fields such as in material sciences for determining the composition, properties, and defects of a material, in the aeronautic, automotive and other manufacturing industries for product development and quality control, and in biomedical research, among others. Specifically, phase-contrast X-ray imaging, and dark-field X-ray imaging have been of growing interest across industries due to the ability to image objects that absorb or reflect very little X-ray light. Further, phase-contrast and dark-filed imaging may be preferred in applications where it is undesirable for the target sample to absorb radiation such as in medical imaging.

Currently, the most developed phase-contrast imaging methods are based on either grating interferometry or speckle tracking. Both methods have been demonstrated to have single-shot capability, tomography compatibility, and the ability to image using synchrotron-level X-ray sources and polychromatic laboratory sources. Single-shot grating-based X-ray imaging (SGXI) and single-shot speckle-based X-ray imaging (SSXI) have been widely applied to biomedical imaging and wavefront sensing. However, SGXI methods using a single grating suffer from low spatial resolution and require a highly transversely coherent radiation source. To achieve higher sensitivity and resolution, SGXI methods require a setup with multiple-gratings and a complicated calibration procedure to eliminate systematic errors. SSXI is a more flexible approach than SGXI and requires less radiation source coherence. However, current SSXI methods also require complicated calibration techniques due to the randomness of the speckle generator, which is usually a piece of sandpaper or membrane filter. Further, SSXI also suffers from a slow data analysis procedure, which makes it unsuitable for real-time measurements Grating-based and speckle-based imaging methods rely on advanced data-analysis algorithms, which require multiple images and/or speckle patterns for generating a high-contrast image. Some single-shot improvements have been proposed, including a speckle tracking method based on the transport of intensity equation (TIE) which can achieve single-shot measurements of weakly absorbing and non-absorbing samples. However, the TIE-based method is limited to imaging single-material samples. While significant improvements have been made in phase-contrast imaging, each method has respective drawbacks including complex optical setups, complicated calibration requirements, long data-acquisition times, long imaging times, and strict requirements of applied radiation, among others.

SUMMARY OF THE DISCLOSURE

An imaging system for performing phase-contrast imaging includes a radiation source configured to provide radiation, along an axis of propagation, to a coded mask. The coded mask is disposed along the axis of propagation and the coded mask has a phase and absorption profile according to pre-determined pattern. The radiation is further impingent on a sample, and a detector system is disposed along the axis of propagation, the detector being configured to detect the radiation and to generate an electrical signal in response to detecting the radiation. The imaging system may further include a processor configured to execute machine-readable instructions that cause the processor to retrieve the electrical signal and to perform a minimization or maximization process such as maximum-likelihood optimization to generate a light-field image of a sample disposed along the axis of propagation. In other examples, the processor may be configured to perform machine learning techniques to generate a light-field image of a sample disposed along the axis of propagation.

A method for performing phase-contrast imaging includes providing radiation, along an axis of propagation, to a coded mask. The coded mask is disposed along the axis of propagation and the coded mask is configured to alter a phase and intensity profile of the radiation according to a pre-determined phase and absorption pattern of the coded mask. A detector system is disposed along the axis of propagation, the detector system configured to detect the radiation and to generate an electrical signal indicative of the detected radiation. The method may further include performing a minimization process, or a maximization process, such as maximum-likelihood optimization to generate a light-field image of a sample disposed along the axis of propagation. Additionally, the method may include performing machine-learning methods for generating a light field image of a sample disposed along the axis of propagation.

BRIEF DESCRIPTION OF THE DRAWINGS

FIG. 1A is a schematic diagram of an embodiment of a coded-mask-based multi-contrast imaging (CMMI) system with a sample positioned after a coded mask.

FIG. 1B is a schematic diagram of an embodiment of a CMMI system with a sample positioned before a coded mask.

DETAILED DESCRIPTION

Figure 2:
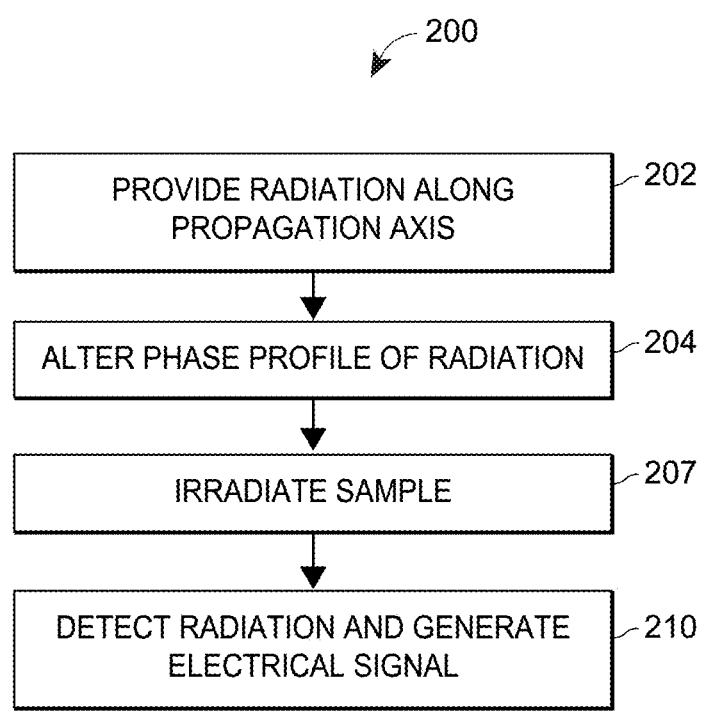
FIG. 2 is a block diagram of a method for performing CMMI.

An ultra-high contrast X-ray imaging system and associated method are disclosed. The disclosed system employs a coded mask having a pre-determined phase and absorption profile to perform coded-mask-based multi-contrast imaging (CMMI). The pre-determined phase and absorption profiles of a coded mask provide an ultra-high contrast pattern, and prior knowledge of the phase and absorption profile enables reference-free single-shot X-ray imaging measurements and the use of machine learning methods. Combined with advanced phase retrieval algorithms and machine learning, the disclosed system and method enable real-time phase contrast imaging that provides increased image contrast and resolution as compared to other imaging techniques. In a specific example, an algorithm based on maximum-likelihood optimization is disclosed for simultaneously reconstructions of absorption-, phase-, and dark-field images. The CMMI method has great potential for real-time quantitative phase imaging and wavefront sensing when combined with deep learning techniques.

The CMMI has advantages over both grating-based and traditional speckle-based phase-imaging methods and thus can be applied to many more applications with better performance. For example, CMMI provides higher spatial resolution and phase sensitivity over longer imaging distances than single-grating interferometry, where the latter is limited by the Talbot effect and the transverse coherence of X-ray source. Additionally, the disclosed CMMI is able to operate across a broader range of X-ray radiation energies than single-grating interferometry systems. Compared to a multi-grating system, the CMMI is simpler to implement and does not require an absorption grating, which is challenging, if not impossible, to fabricate for high energy X-rays (i.e., on the order of tens of keV). Overall, CMMI requires less X-ray coherence and intensity than other grating-based phase-contrast imaging methods and the described methods may also be implemented in tomography systems. Further, the CMMI methods may be performed in both single-shot and step-scanning measurements requiring less images than other scanning methods and providing better phase sensitivity and sub-pixel spatial resolution.

Traditional speckle-based phase-contrast imaging methods are limited by the requirement of a random speckle generator, such as a piece of sandpaper or membrane filter, which requires complicated calibration. By contrast, the CMMI employs a pre-designed random mask, allowing for prior knowledge of a phase and absorption profile, to generate higher contrast speckle images. Thus, the CMMI enables reference-free measurements. The imaging techniques described reconstruct the phase and intensity change of radiation due to a sample by determining changes in the speckle pattern generated by the coded mask.

The CMMI allows for the use of advanced data-analysis algorithms such as maximum-likelihood and machine learning analysis for real-time measurements, which is not optimal using traditional grating-based and speckle-based imaging methods. The described CMMI enables multi-contrast imaging to provide superior performance, including higher resolution, faster imaging, and easier implementation than other phase-contrast imaging techniques. Therefore, CMMI has a broader range of applications including medical imaging, wavefront sensing, material characterization, quality control and security detection, microelectronics, semiconductor industries, clinical facilities, and others.

FIGS. 1A and 1B are schematic diagrams of embodiments of CMMI systems as described herein. FIG. 1A illustrates a CMMI system 100 with a sample positioned after a coded mask, while FIG. 1B illustrates a CMMI system 120 with a sample positioned before a coded mask. Both CMMI systems 100, and 120 of FIGS. 1A and 1B include a radiation source 102, a coded mask 105, and a detector system 108. The radiation source 102 is configured to provide radiation 103 along a propagation axis A. The radiation 103 is a light beam having an intensity profile, and a phase profile. In embodiments, the light beam may include one or more of a Gaussian beam, a plane wave, a Bessel beam, or another beam of radiation having an intensity profile and a phase profile. In embodiments, the beam may have a predetermined intensity profile and phase profile. A sample 110 may be positioned along the propagation axis A after, or before the coded mask 105, as illustrated in FIGS. 1A and 1B respectively. The coded mask 105 is disposed along the propagation axis A such that the radiation 103 is impingent on the coded mask 105. The coded mask 105 has a phase and absorption mapping, and the coded mask 105 alters the phase and intensity profile of the radiation 103 according to the phase and absorption mapping of the coded mask 105. The detector system 108 may include one or more optical elements for guiding and/or manipulating the radiation 103. Further, the detector system 108 includes one or more detectors configured to detect the radiation 103, the one or more detectors further configured to generate a signal indicative of the detected radiation. The signal may then be processed to determine light field and dark field images of the sample 110. Light field images may include horizontal phase contrast images, vertical phase contrast images, composite phase contrast images, transmission images, direct detection images, homodyne or heterodyne detection images, or other types of images of the sample 110.

FIG. 2 is a block diagram of a method 200 for performing CMMI. The method 200 may be performed by either of the CMMI systems 100 and 120 of FIGS. 1A and 1B, or by another imaging system. As shown in FIGS. 1A and 1B, the sample 110 may be positioned along the propagation axis A either after, or before the coded mask 105. Referring now simultaneously to FIGS. 1A, 1B, and 2 the method 200 includes providing the radiation 103 by the radiation source 102 along the propagation axis A (block 202). The radiation 103 may be X-ray radiation or another type of radiation for performing imaging of the sample 110. In embodiments, the radiation 103 may have energies of 1 keV, 100 keV, 100 eV to 1 keV, 500 eV to 5 keV, 5 keV to 30 keV, 30 keV to 100 keV, 100 keV to 1000 keV, or above 1000 keV. The radiation source 102 may include one or more of a bend magnet, an undulator, a wiggler, a cyclotron, a synchrotron, a free electron laser (FEL), a compact synchrotron light source, a laboratory X-ray source, a microfocusing laboratory X-ray source, a stationary anode X-ray tube, a rotating anode X-ray tube, a microstructured-target X-ray emitter, a multi-target X-ray source, a liquid-metal jet X-ray source, a laboratory X-ray source, a gamma ray source, a linear accelerator (LINAC), a higher order harmonic generation source, or another radiation source.

In the embodiment of FIG. 1A, the radiation 103 propagates along the propagation axis A and the radiation 103 is incident on the coded mask 105. The coded mask 105 alters the phase and intensity profile of the radiation 103 according to a known phase and absorption map of the coded mask 105 (block 204). The phase, absorption and dark-field signal of the sample 110 can be obtained using the measured images with sample 110 and without sample 110. Prior knowledge of the phase and absorption applied by the coded mask 105 allows for the reference-free measurement as well, where only the images with sample 110 are measured. The coded mask 105 may be a binary mask having pixels with each pixel configured to alter the phase of a wavefront of radiation by either 0° or 180°. In embodiments, the coded mask 105 may be a binary phase mask with pixels that alter the phase of a wavefront by any two different amounts from 0° to 360°. The coded mask 105 may be a phase mask that alters the phase of a wavefront by any (e.g., multi-level, continuous, random, or pseudo-random) amounts. The coded mask 105 may be a phase/absorption mask that alters the phase and intensity of a wavefront by any (e.g., two, multi-level, continuous, random, or pseudo-random) amounts. Further, in embodiments, the coded mask 105 may include one or more of an aperture, a plate, a waveplate, a spatial light modulator, a grid, a grating, or another element capable of providing a phase and/or absorbing radiation.

The method 200 further includes radiating the sample 110. In FIG. 1A, the radiation 103 propagates along the propagation axis A and the radiation irradiates the sample 110 (block 207). The sample 110 further alters the phase and intensity profile of the radiation 103 according to material properties and geometric properties of the sample 110. For example, a thickness, height, width, density, scattering, shape, and one or more indices of refraction of the sample 110 may all contribute to the change in the phase and intensity profile of the radiation 103. Due to the known phase and absorption applied by the coded mask 105, the phase and intensity difference due to the sample 110 may be determined through image processing and analysis. The thickness, type of material, shape, and other properties of the sample may be determined from the detected intensity profile of the radiation 100. In examples, the sample 110 may be partially or completely transparent to the radiation 103. As previously discussed, the sample 110 may be disposed along the propagation axis A before the coded mask 105, and therefore, the radiation may first radiate the sample 110 (block 207) before the radiation is incident on the coded mask 105 (block 204).

The radiation 103 propagates further along the axis A and the detector system 108 detects the radiation 103 and generates an electrical signal indicative of the intensity profile of the radiation 103 (block 210). In embodiments, the detector system 108 may include an X-ray sensor, a heterodyne sensor, a homodyne sensor, a CCD camera, a CMOS camera, a photon-counting detector, and any 1D or 2D image detectors. In embodiments, the detector system 108 may include one or more mirrors, lenses, gratings, scintillators, waveguides, polarizers, waveplates, spatial filters, beam splitters, spectral filters, and any optical elements for guiding and/or manipulating the radiation.

Figure 3A:
FIG. 3A is an illustration of a binary coded mask having pixels according to a pre-determined phase and absorption pattern.

FIG. 3A is an illustration of an embodiment of a design pattern of a phase map 310 of a binary coded-mask 300 having pixels 305. The coded mask 300 may be implemented as the coded mask 105 of FIGS. 1A and 1B. The phase map 310 was generated by a processor executing computer executable instructions that cause the processor to generate a two-dimensional randomized binary pattern which was then converted to a pattern for the fabrication process. The pixels 305 form the phase map 310 of the coded mask 300, and each of the pixels 305 is independently configured to alter the phase of a wavefront of radiation by one of two values, a low-phase value and a high-phase value, as illustrated by the white and black pixels respectively. For simplicity and clarity, the pixels 305 will be referred to herein as low-phase pixels or high-phase pixels according to the phase imbued by the pixel. The phase map 310 of the pixels 305 of the coded mask 300 is pre-designed and, therefore, the coded mask 300 alters the phase of a wavefront according to known amounts, determined by the energy of radiation 103. The coded mask 300 also alters the intensity of a wavefront according to known amounts.

The phase map 310 of the coded mask 300 of FIG. 3A was generated with each pixel having a 50% probability (i.e., 50/50 probability) of being a low-phase pixel or a high-phase pixel, wherein a low-phase pixel alters the phase of a wavefront by a lower phase amount and a high-phase phase pixel alters the phase of a wavefront by a higher phase amount relative to the low-phase pixel. In embodiments, the binary coded mask 300 may be randomly generated with low-phase to high-phase pixel probabilities of 10/90, 20/80, 30/70, 40/60, 50/50 or another probability. In embodiments, the phase map 310 of the coded mask 300 may be a multi-level profile with pixels 305 configured to alter the phase of a wavefront according to a pre-designed phase pattern. In embodiments, the phase map 310 of the coded mask 300 may be a continuous profile with pixels 305 configured to alter the phase of a wavefront according to a predesigned phase pattern. Further, in embodiments, the mask 300 may include one or more pixels 305 configured to alter an amplitude profile of a wavefront (e.g., pixels that partially absorb, entirely absorb, refract, transmit, reflect, etc. radiation).

Figure 3B:
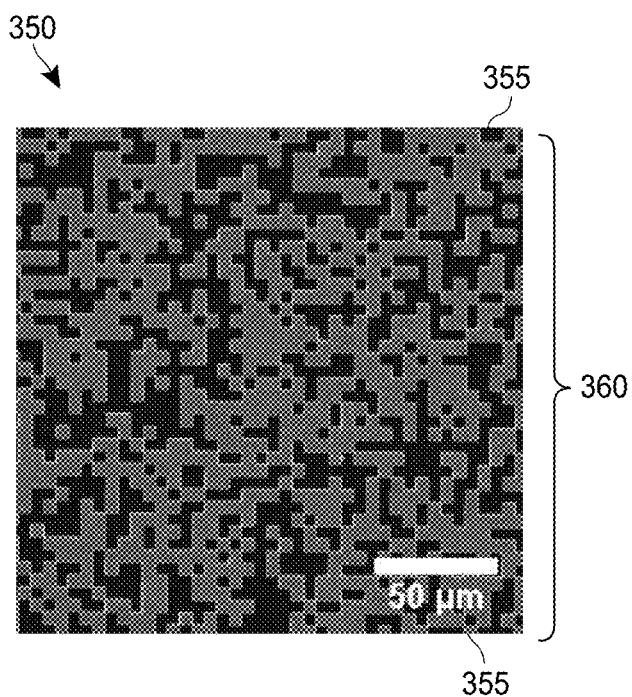
FIG. 3B is a scanning electron microscope (SEM) image of a fabricated binary coded mask.

FIG. 3B is a scanning electron microscope image of a fabricated binary coded mask 350 with pixels 355. The pixels 355 together form a SEM image map 360 of the binary coded mask 350. Each of the pixels 355 of the binary coded mask 350 is a square with a height and width of 5 microns in each dimension. In embodiments, the pixels 355 may be square, rectangular, triangular, circular, or another shape with dimensions on the order of 0.1 to 1 micron, 1 to 5 microns, 5 to 10 microns, or greater than 10 microns. The size of the pixels 355 determines a resolution of the CMMI method which may be limited by an imaging resolution of a detector system configured to detect a wavefront, such as the detector system 108 of FIGS. 1A and 1B. Further, the pixels 355 may form an image map 360 with an array of 10×10 pixels, 50×50 pixels, 100×100 pixels, 250×250 pixels, 500× 500 pixels, 1000×1000 pixels, or another number of pixels. Additionally, the number of pixels in each dimension the image map 360 may differ (e.g., a 100×200 pixel array, 50×500 pixel array, or another pixel array).

The binary coded mask 350 was fabricated by applying a layer of resist to a silicon wafer with membrane windows made of a window membrane, and performing electron beam lithography to selectively remove the resist after immersion in a developer solution to create a mold. Gold was electroplated into the mold and the mold was removed resulting in the binary coded mask 350 with gold pixels as the high-phase pixels. The pixels on the window membrane that are not covered by the gold pixels are the low-phase pixels. The window membrane is composed of silicon nitride with a thin layer of titanium and gold to act as the base electroplating layer. In embodiments, the coded mask 350 may be fabricated via wet etching, dry etching, electron beam lithography, electroplating, chemical assisted etching, laser ablation, 3D printing, or another fabrication technique. Further, the coded mask 350 may include one or more materials including gold, nickel, copper, silicon, bismuth platinum, an electrically and/or optically active metal, a semiconductor material, diamond, a polymer, or another material that may be determined by an energy of radiation of an imaging system. One or more of the materials of the coded mask 350, and/or the thickness of the coded mask 350, may be selected to create sufficient intensity contrast (>1%) on the detector for the CMMI reconstruction. In embodiments it may be desirable for the coded mask 350 to have a high thermal conductivity. For example, in high power beam systems it may be preferable for the coded mask 350 to include a material such as diamond with a thermal conductivity greater than 100 W/(m·K). The method and materials used to fabricate the coded mask 350 may depend on a desired thickness and size of the coded mask 350, a desired size of the pixels 355, available fabrication methods, and/or a desired performance of the coded mask 350 (e.g., contrast, resolution, distortion amount, etc.). For example, electron beam lithography was used to fabricate the binary coded mask 350 of FIG. 3B to achieve a desired phase contrast of the phase map 310, and with a suitable lithographic resolution to avoid edge effects.

Figure 4A:
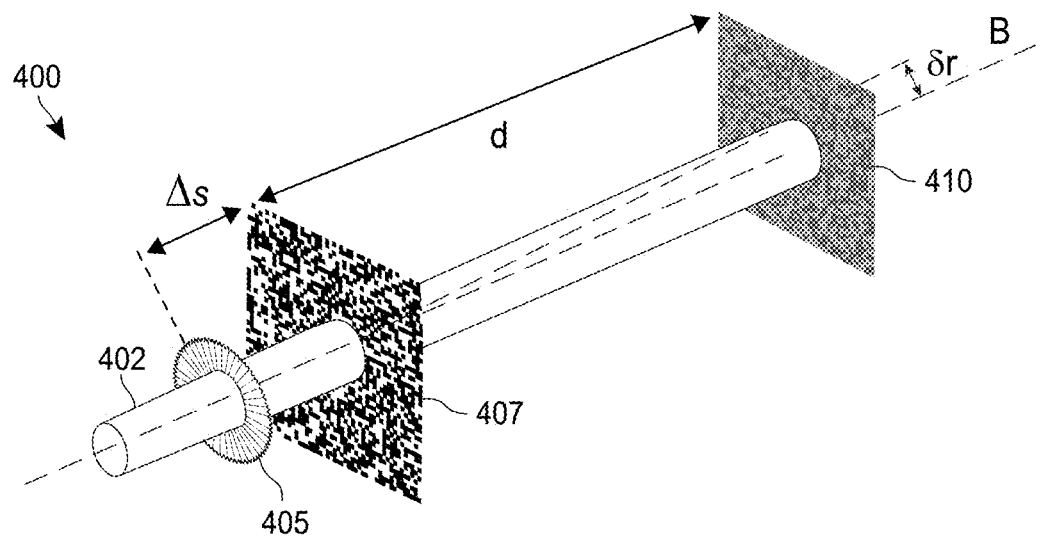
FIG. 4A is a schematic diagram of a collimated beam configuration for performing CMMI.
Figure 4B:
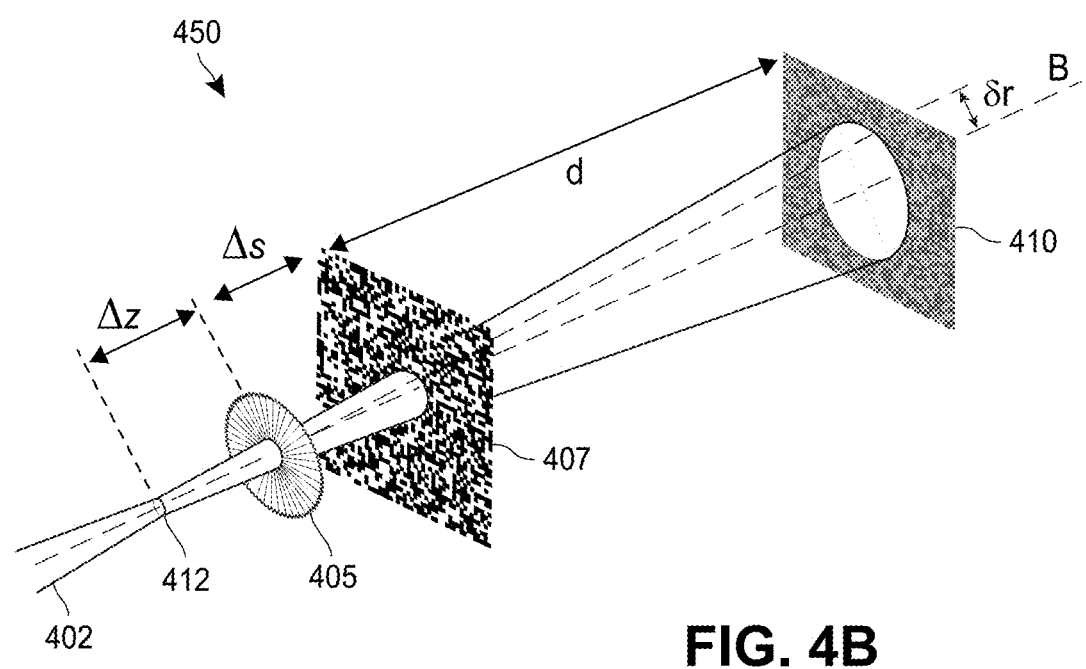
FIG. 4B is a schematic diagram of a divergent beam configuration for performing CMMI.

FIGS. 4A and 4B are schematics of an arrangement of optics for performing CMMI for a collimated beam configuration 400 and a divergent beam configuration 450, respectively. Each of the collimated and divergent beam configurations 400 and 450 include radiation 402 propagating along an axis of propagation B, a sample 405 disposed along the axis B, a coded mask 407 disposed along the axis B, and a detector 410 disposed along the axis B configured to receive and detect the radiation 402 at one or more sensors of the detector 410. The sample 405 is disposed along the axis B such that the radiation 402 is incident on a portion, or the entirety, of the sample 405 for performing CMMI of the sample 405. FIGS. 4A and 4B include some relevant geometric parameters for determining an image from the radiation detected by the detector 410, including the distance from a beam focus 412 to the sample 405, $\Delta z$, the distance between the sample 405 and the coded mask 407, $\Delta s$, and the distance from the mask 407 to the detector 410, d. In the embodiments, the sample 405 may be placed after the coded mask 407 in both configurations 400 and 450 of FIGS. 4A and 4B. In other embodiments, other parameters may be used. For one example, performing optical and geometric analysis using a different coordinate space (e.g, polar space, Fourier space, etc.) may require different sets of relevant parameters for performing CMMI as described herein. Additionally, a person of ordinary skill in the art will recognize that other parameters may be used for performing the analysis for the given configurations 400 and 450 of FIGS. 4A and 4B. In some embodiments, $\Delta z$ may be on the order of centimeters to tens of centimeters, or further, on the order of meters, $\Delta s$ may be on the order of tenths of a centimeter to centimeters or tens of centimeters, and d may be on the order of tens of centimeters to several meters.

The coded mask 407 alters the phase and intensity of the radiation 402 according to a speckle pattern of the coded mask 407. The speckle pattern of the coded mask 407 may be applied to the phase and intensity of the radiation 402 by pixels disposed on a surface of the coded mask 407. As such, the surface of the coded mask having the pixels must be configured for the radiation 402 to impinge upon the pixels. For example, the surface having the pixels may be generally orthogonal to the axis B, or at an angle relative to the axis B, to imbue the speckle pattern onto the phase and intensity of the radiation 402. In embodiments, the coded mask 407 may be rotated or shifted in reference to the axis B to provide multiple shots with different speckle patterns imbued onto the phase and intensity of the radiation 402. The speckle pattern may be known or predetermined by a mapping of the coded mask 407, such as the known 50/50 pixel mapping of the phase map 310 of FIG. 3A. The sample 405 further alters the radiation 402 according to optical and geometric properties of the sample 405. The detector 410 then detects the radiation 402 and a maximum likelihood minimization process may be implemented to perform CMMI as described herein.

The speckle pattern that is applied to the radiation 402 by the coded mask 407 is further modified by the absorption, phase, distortion, and scattering of the sample 405. The radiation 402, altered by both the coded mask 407 and the sample 405, has a beam intensity profile $I_s(r')$ that can be expressed in terms of the intensity profile of radiation 402 altered by the coded mask 407 only, $I_r(r)$, with r' being pixel displacement due to the sample 405, defined by $r'=r+\delta r$. Under the small angle approximation, $\delta r$ is related to a phase distortion profile of the sample, $\nabla \phi(r)$ by $$\delta r = \frac{\alpha \lambda d}{2\pi} \nabla \phi(r). \qquad \text{EQ. 1}$$

The phase distortion profile of the sample is indicative of the optical and structural properties of the sample to be imaged, with $\lambda$ being a wavelength of the radiation, and with $\alpha$ being a geometric scale factor that is dependent on the specific optical setup of the CMMI system. In configurations having the sample 405 downstream of the coded mask 407, such as the configuration 100 of FIG. 1A, the factor $\alpha$ is set to a value of 1, and the distance d becomes the distance from the sample 405 to the detector 410. In configurations having the sample 405 before the coded mask 407, such as the configuration 120 of FIG. 1B, the factor α is given by L/(L+Δs) with L being the distance from the source 102 to the sample 110 and Δs being the distance from the sample 110 to the coded mask 105. In the setup with a diverging beam 402 of FIG. 4B, the factor α is Δz/(Δz+Δs).

Within a detection region on the detector 410, the irradiance of the radiation, with and without the sample 405 disposed along the propagation axis B, is conserved taking into account any absorption and phase due to the sample 405. Therefore, the irradiance at the detector 410 can be expressed as $$I_s(r')dr' = A(r)I_r(r)dr, \qquad \text{EQ. 2}$$

where $A(r)$ is the intensity transmission function of the sample and $I_s(r')$ is the intensity of the radiation after the sample along the propagation axis B. Combining EQ. 2 with the following derivative of EQ. 1

$$dr' = \left[1 + \frac{a\lambda d}{2\pi}\nabla^2 \phi(r)\right]dr = C(r)dr, \qquad \text{EQ. 3}$$

yields the expression, $$I_s(r') = \frac{A(r)I_r(r)}{C(r)}. \qquad \text{EQ. 4}$$

The transmission of the sample 405, for a given region of the sample 405, is therefore a combined effect of the absorption of the sample 405, represented by $A(r)$, and a lens effect of the phase modulation, $C(r)$, which contains the phase term $\phi(r)$ of the sample 405. A dark-field image signal, $D(r)$, can then be derived from EQ. 4 as $$I_s(r') = \frac{A(r)}{C(r)}\{\bar{I}_r(r) + D(r)[I_r(r) - \bar{I}_r(r)]\}, \qquad \text{EQ. 5}$$

where $\bar{I}_r(r)$ is a local regional average of $I_r(r)$.

A maximum-likelihood process was then developed to determine profiles for the phase of the sample 405, absorption of the sample 405, and dark-field signal of the sample 405 as represented by ϕ, A, and D, respectively. The profiles for ϕ, A, and D, are determined by a best fit to the measured data of the system, $I_s^m$, by an iterative minimization procedure. The statistical fluctuations of the CMMI systems described herein are generally dominated by Poisson noise. As such, a cost function for determining the desired profiles is $$L_p = \Sigma_{i,j}\{I_s(A,\phi,D) - I_s^m \log[I_s(A,\phi,D)]\} \qquad \text{EQ. 6}$$

where $I_s(A, \phi, D)$ is an estimated speckle pattern of the sample 405 according to EQ. 5, and with i and j being pixel indices in the horizontal and vertical directions of the detector 410.

To enable greater contrast and greater resolution images of the sample 405, signal noise was further suppressed and a total variation regularization represented as $$L_v(f) = \Sigma_{i,j}\sqrt{|f_{i+1,j} - f_{i,j}|^2 + |f_{i,j+1} - f_{i,j}|^2}. \qquad \text{EQ. 7}$$

Resulting in a final form of the total cost function being $$L_t = L_p + \alpha L_v(\|\nabla D\|_2) + \alpha L_v(\|\nabla A\|_2) + \beta L_v(\nabla^2 \phi), \qquad \text{EQ. 8}$$

where $\|\cdot\|_2$ denotes an $l_2$ norm with α and β being regularization weight factors.

An auto-differential (AD) method was implemented to directly calculate a gradient of the cost function $L_t$, and the Adam nonlinear optimization method was applied to determine A, ϕ, and D simultaneously by minimizing EQ. 8. While the Adam nonlinear optimization was implemented, it is envisioned that other nonlinear optimizations may be used, for example, mean-square-root minimization, nonlinear conjugate gradient (NLCG), Broyden-Fletcher-Goldfarb-Shanno (BFGS), Levenberg-Marquardt algorithm, iterating direction method of multipliers (ADMM), or another nonlinear optimization.

Using EQS. 5 and 8, the disclosed maximum-likelihood process enables a pixel-wise reconstruction of the phase profile of the sample 405. With a detector pixel size of p, the phase sensitivity of the described CMMI systems and maximum-likelihood method is estimated to be $p^2/d$ (i.e., the pixel size square divided by the distance from the coded mask 407 to the detector 410). The unique distribution of the coded mask 407 allows for the maximum-likelihood method to achieve high-resolution single-shot measurements. The described pixel-wise displacement reconstruction algorithm is based on maximum-likelihood optimization and auto-differential method, which gives much higher resolution and sensitivity than a correlation-based method. Further, the designed pattern of the coded mask 407 allows the implementation of state-of-the-art machine learning algorithms for real-time analysis for CMMI systems. While the above example is described using nonlinear methods for performing phase reconstruction, phase reconstruction may also be performed using a similarity-comparison method based on cross-correlation algorithm, singular value decomposition (SVD), discrete Fourier transform (DFT), and discrete wavelet transform, or another phase reconstruction method or tool.

The disclosed CMMI systems and methods were implemented according to the configuration of the CMMI system 120 illustrated in FIG. 1B. In the implementation, the radiation source 102 was an X-ray source and a monochromator was configured to filter the radiation 103 to provide 14 keV radiation. Two setups were demonstrated according to the configurations of FIGS. 4A and 4B, which will be referenced in the following discussion of example CMMI systems. In the setup according to the configuration of FIG. 4A, the sample-to-mask distance, Δs, was set to 134 mm, the mask-to-detector distance, d, was set to 310 mm, and the source-to-sample distance, L, was set to 34 m. A setup according to the configuration of FIG. 4B was also implemented using a compound refractive lens to focus the radiation 402 to a beam focus 412, and Δz was set to 134 mm, Δs was set to 75 mm, and d was set to 790 mm, resulting in a geometric magnification of 4.8 for the coded mask 407 and 7.5 for the sample 405 at an imaging plane of the detector system 410. For both example CMMI systems, the detector system 410 included a 100 µm thick LuAG:Ce scintillator, a 10× objective lens, and an Andor Neo sCMOS camera configured to detect the radiation 402. The effective pixel size of all recorded images was 0.65 µm and the estimated resolution of the detector system was 2.2 µm.

The coded mask 407 was a binary coded mask with a pattern thickness of 2 µm that was fabricated by electroplating Au into polymer molds (poly(methyl methacrylate), PMMA) on a silicon nitride membrane. The coded mask pattern had a binary pixel size of 5 µm and a bias-corrected pattern. Further, the coded mask pattern was generated using a Python program with a random number generator to create a script for a CNST Nanolithography Toolbox.

Figure 5A:
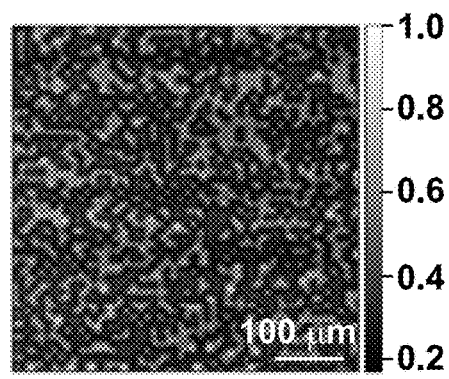
FIG. 5A is an image of a reference speckle pattern generated by a coded mask.
Figure 5B:
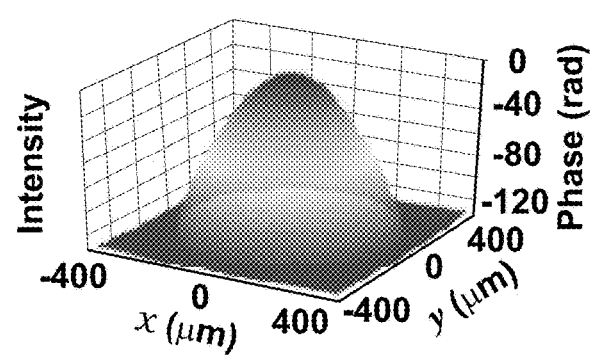
FIG. 5B is a plot of reconstructed phase for CMMI of a beryllium lens.
Figure 5C:
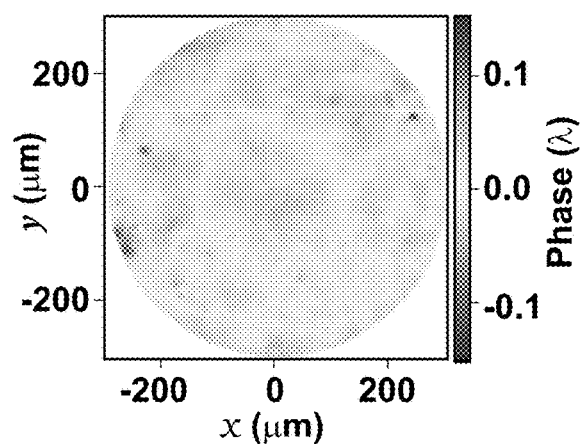
FIG. 5C is a plot of residual phase error for CMMI of a beryllium lens.
Figure 5D:
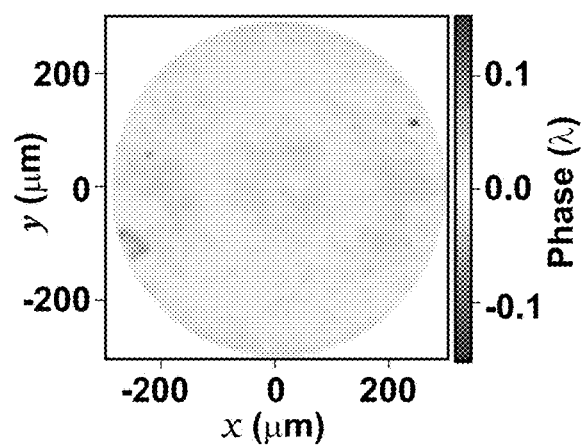
FIG. 5D is a plot of reconstructed residual phase error of a scanning speckle vector tracking image of a beryllium lens.

A beryllium lens with an apex radius of 200 µm was first measured using the CMMI system 400 setup of FIG. 4A without geometric magnification. During phase reconstruction of the image of the beryllium lens, maximum-likelihood optimizations with three hundred iterations were performed with the regularization weight factors, $\alpha$ and $\beta$, set as 10 and 0.1, respectively. FIG. 5A is a transmission image of a reference speckle pattern generated by the coded mask 407. The average contrast of the reference speckle pattern, as defined by the ratio between the standard deviation and mean value of the pattern intensity, is approximately 30%, which is much higher than image contrasts from other phase contrast methods, such as sand-papers and membrane filters for example. The demonstrated high pattern contrast improves the noise robustness and the phase retrieval accuracy of the disclosed CMMI systems. FIGS. 5B and 5C are plots of the reconstructed phase, $\phi$, and residual phase error, respectively, after removing a best fit parabola. The beryllium lens was also measured by a traditional scanning speckle vector tracking (XSVT) method with a 10×10 scan point pattern. FIG. 5D is a plot of the reconstructed residual phase error of an image of the beryllium lens using the XSVT method. The relative difference between the residual phases in of the CMMI and XSVT methods is $0.012\lambda$ $\lambda$ (RMS), which is beyond the sensitivity of the example CMMI setup as given by $$\frac{p^2}{d} = 0.015\ \lambda.$$

Figure 6A:
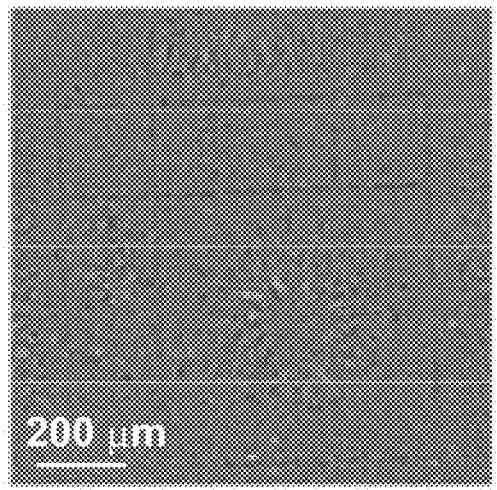
FIG. 6A is an image of reconstructed phase results of a test sample obtained by traditional X-ray speckle-tracking imaging.
Figure 6B:
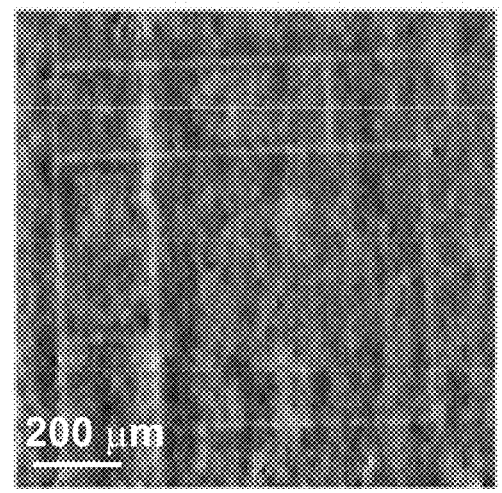
FIG. 6B is an image of reconstructed phase results of a test sample obtained by X-ray single-grating interferometry imaging.
Figure 6C:
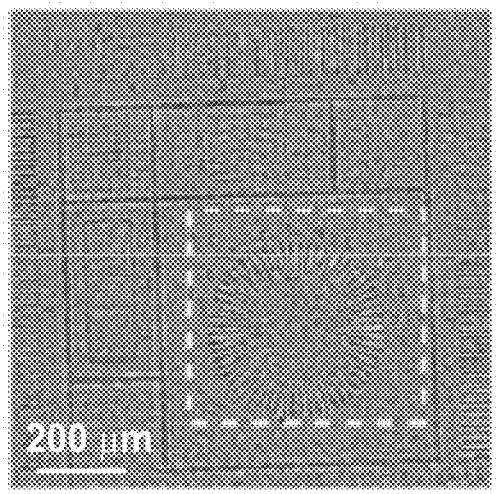
FIG. 6C is an image of reconstructed phase results of a test sample obtained by CMMI.
Figure 6D:
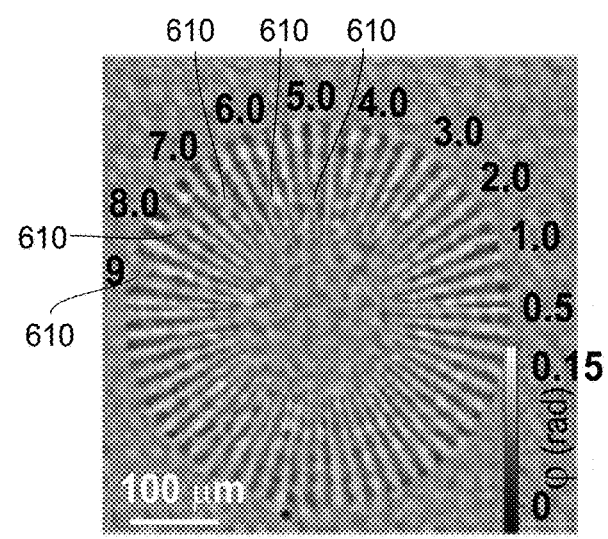
FIG. 6D is an enlarged region of the reconstructed phase image in FIG. 6C obtained by CMMI.

The spatial resolution of the disclosed CMMI method and systems was demonstrated by measuring a standard test sample and comparing the reconstructed CMMI images with images from single-shot X-ray grating interferometry (XGI) and correlation-based X-ray speckle-tracking (XST) methods. FIGS. 6A through 6C are images of reconstructed phase results as obtained, respectively, by the XST method, the XGI method, and the CMMI method. FIG. 6D is an image of an enlarged region of the image of FIG. 6C. FIG. 6D includes reference resolution values at the edges of radial lines of the image, and gaps 610 in the radial lines. A visible gap 610 in lines of the radial lines may be used to estimate the resolution of the image by determining the smallest distinguishable gap 610, and referencing a corresponding resolution value in micrometers. For example, the gaps 610 are readily visible at image resolutions of 9, 8.0, 7.0, 6.0, and 5.0 micrometers, while the gaps are less resolvable at 4 micrometers and smaller. Both the XST and CMMI methods employed a coded mask while the XGI method used a checkerboard $\pi/2$ grating with a pattern period of 3.4 µm. The spatial resolution of the CMMI method was determined to be significantly better than the XST and XGI methods due to the use of the coded mask and the maximum-likelihood reconstruction. The spatial resolution of the CMMI method, further defined as the smallest resolvable line pair in the Siemens star pattern in FIG. 6D, was determined to be 3.8 µm. The spatial resolution is greater than the pixel size because of the combined contributions of the detector resolution (i.e., 2.2 µm) and aberrations and instabilities of the beamline optics.

As previously described, a CMMI system with higher spatial resolution was constructed according to the configuration of FIG. 4B by incorporating geometric magnification and using a divergent beam. A Siemens star test sample with 100 nm structures was measured using the CMMI technique. FIGS. 7A-7E are the resultant images from the CMMI technique for horizontal differential phase, vertical differential phase, composite phase, dark-field, and transmission, respectively. The recovered spatial resolution for the phase images of 7A-7E, at the sample plane, was 750 nm, which is consistent with the estimation of the resolution as measured in FIGS. 6C-6D with taking the magnification factor of 4.8 into account.

Figure 7A:
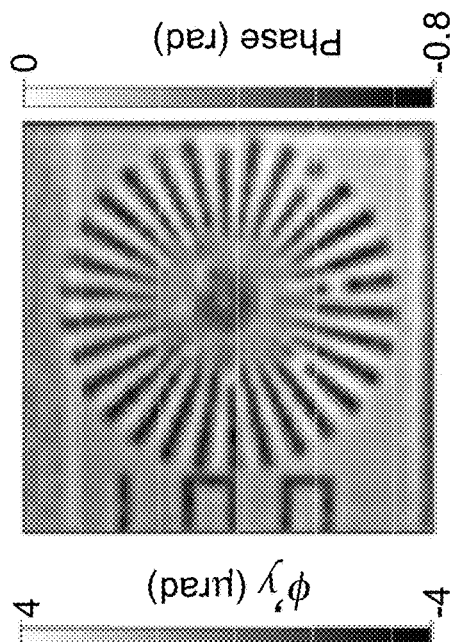
FIG. 7A is a horizontal differential phase image of a test sample as obtained by CMMI
Figure 7B:
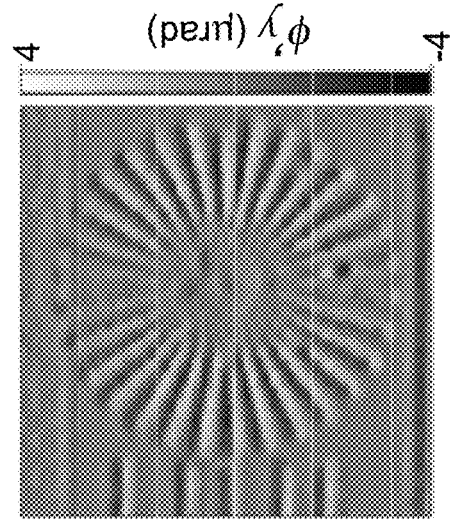
FIG. 7B is a vertical differential phase image of a test sample as obtained by CMMI.
Figure 7C:
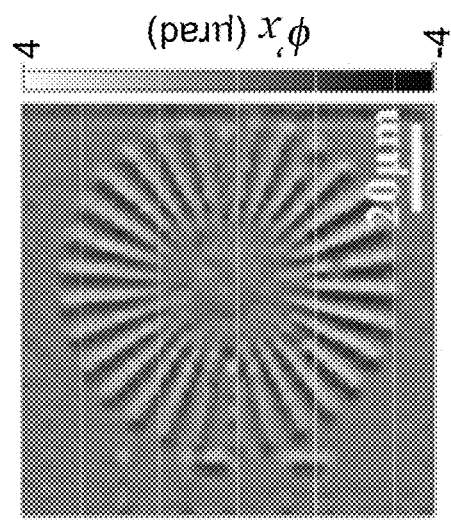
FIG. 7C is a composite phase image of a test sample as obtained by CMMI.
Figure 7D:
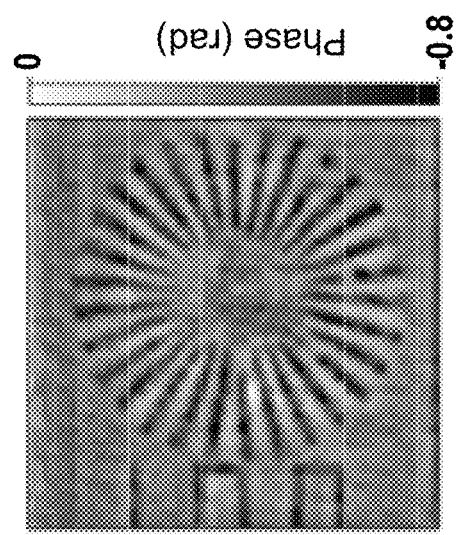
FIG. 7D is a dark-field image of a test sample as obtained by CMMI.
Figure 7E:
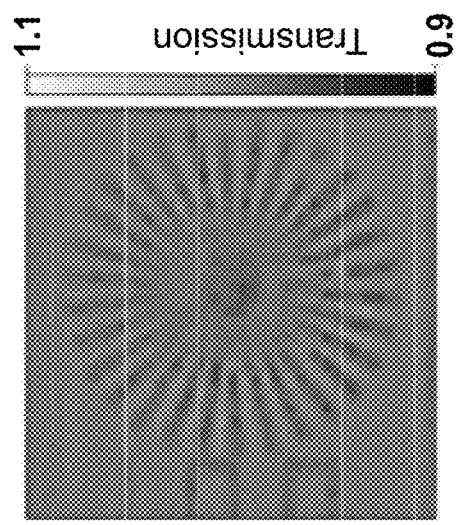
FIG. 7E is a transmission image of a test sample as obtained by CMMI.
Figure 7F:
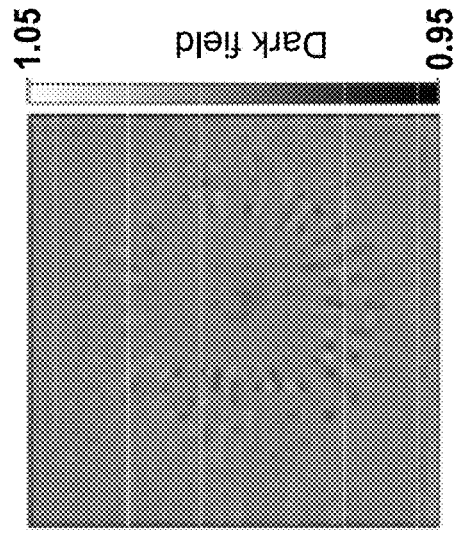
FIG. 7F is a phase image reconstructed by a modified deep-learning method based on a pyramid, warping, cost (PWC) net model.

The use of a coded mask as described herein, enables real-time phase-contrast imaging to be combined with deep-learning techniques. A training set of 5000 images were simulated from the known pattern of the coded mask and randomly generated phase distortions were added to the images using a low-pass filter. FIG. 7F is a phase image that was reconstructed by a modified deep-learning method based on a pyramid, warping, cost (PWC) net model. The image quality and spatial resolution of FIG. 7F is approximately 1 µm. The calculation for the deep learning method was 0.5 s, which is a factor of 56 improvement as compared with the maximum-likelihood method used herein. The demonstration of utilizing machine learning in phase-contrast imaging illustrates a unique feature of the coded mask and the CMMI systems disclosed. The use of machine learning for phase image reconstruction provides immense potential for advancements in real-time single-shot phase-contrast imaging and wavefront sensing applications. Further, the use of machine learning would not be viable without prior knowledge of the phase/absorption mapping of the coded mask.

Figure 8:
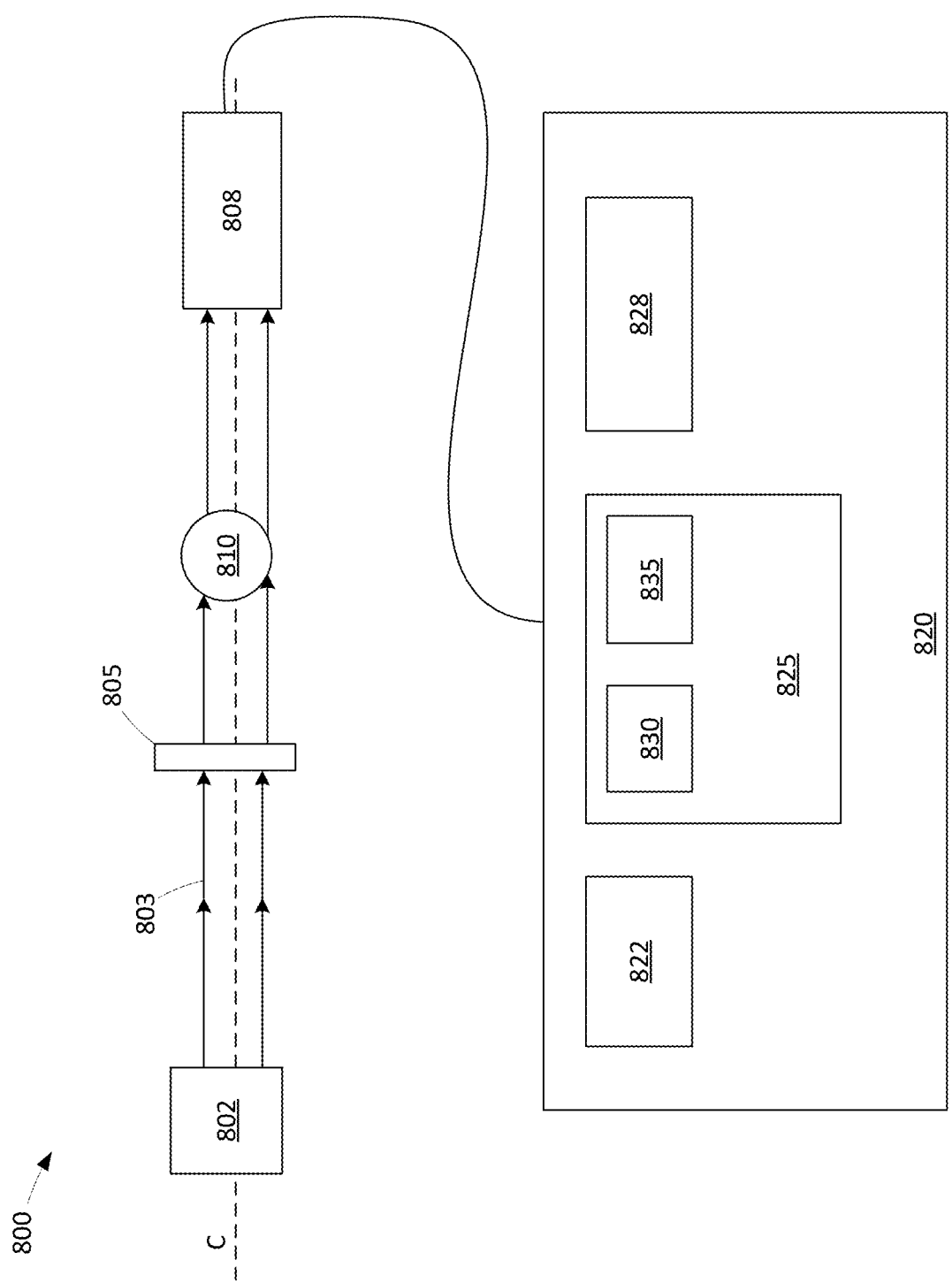
FIG. 8 is a block diagram of an embodiment of an optical system for performing CMMI including a processing unit.

FIG. 8 is a block diagram of an embodiment of an optical system 800 for performing CMMI as described herein. The system 800 includes a radiation source 802, a coded mask 805, a detector 808 and a processing system 820. The radiation source 802 is configured to provide radiation 803 along an optical axis C. The coded mask 805 is disposed along the optical axis C, with the coded mask 805 physically configured to alter the phase and intensity of a radiation 803 according to the phase and absorption map of a coded mask 805. A sample 810 may be disposed along the optical axis C before or after the coded mask 805 for performing imaging of a portion, or the entirety of the sample 810. The radiation 803 is incident on the sample 810, and the radiation 803 is then incident on the detector 808. The detector 808 is disposed along the optical axis C, the detector 808 being configured to receive the radiation 803 and to generate an electrical signal indicative of the received radiation. The detector 808 may be communicative coupled to processing system 820, with the detector configured to provide the electrical signal indicative of the received radiation to the processing system 820. The detector 808 may communicate with the processing system 820 via any suitable communication means, including by wired and/or wireless connectivity components that implement one or more communication protocol standards like, for example, TCP/IP, WiFi (802.11b), Bluetooth, Ethernet, or any other suitable communication protocols or standards.

In embodiments, the processing system 820 may include a central processing unit 822 (CPU, GPU, and/or tensor processing unit (TPU)), one or more memories 825, and/or a controller 828. The controller 828 may include hardware and/or software configured to control components of the optical system 800. For example, the controller 820 may be configured to control the operation of the radiation source 802, control a position or scanning angle of the coded mask 807, control a position or angle of the sample 810, and/or control the operation and retrieval of signals from the detector 808. The one or more memories 825 may include any machine-readable storage medium (e.g., a platter of a hard disk drive, a digital versatile disc, a compact disc, flash memory, read-only memory, random-access memory, etc.) on which machine-readable instructions (e.g., program code in the form of, for example, software and/or firmware) are stored for any suitable duration of time. The one or more memories 825 may store data 830 indicative of the electrical signals provided by the detector 808. The one or more memories 825 may further store machine-readable instructions 835. The machine-readable instructions 835 may include processes and any requisite data for performing a phase reconstruction, a minimization process, a maximization process, a maximum-likelihood optimization, a machine-learning method, similarity comparison, cross-correlation comparison, image filtering, graphic processing techniques (e.g., high pass filtering, low pass filtering, bandpass filtering, chromatic filtering, sharpening, blurring, image patching, image parsing, image alignment, cropping, subpixel shifting, downsampling, up-sampling, smoothing, etc.) The central processing unit 822 may be configured to access the data 830 and to execute the machine-readable instructions 835 stored in the one or more memories 825 to perform the CMMI methods described herein.

Figure 9A:
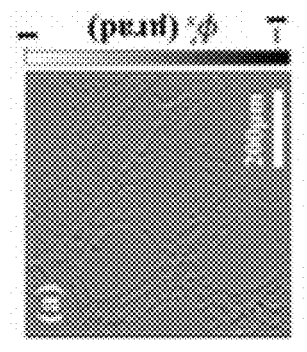
FIG. 9A is a reconstructed horizontal differential phase X-ray image of an elytra of a beetle.
Figure 9B:
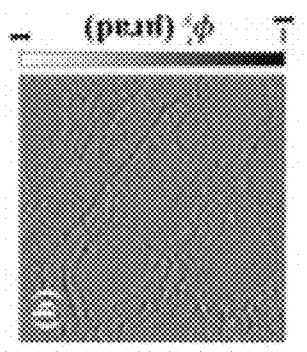
FIG. 9B is a reconstructed vertical differential phase X-ray image of an elytra of a beetle.
Figure 9C:
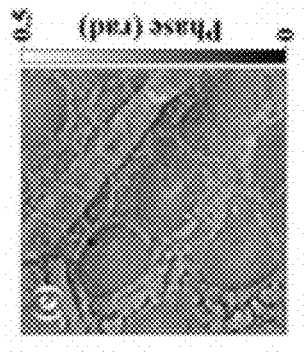
FIG. 9C is a phase reconstruction X-ray image of an elytra of a beetle.
Figure 9D:
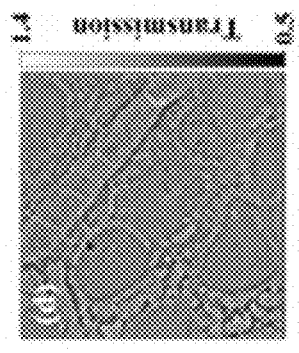
FIG. 9D is an X-ray transmission image of an elytra of a beetle.
Figure 9E:
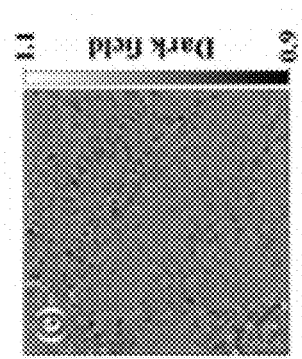
FIG. 9E is a dark-field X-ray image of an elytra of a beetle.

The systems and methods described herein were implemented to image an elytra of a Namib desert beetle. FIGS. 9A-9E are reconstructed X-ray images of the elytra of a Namb desert beetle. The images of FIGS. 9A-9E were obtained using an undulator as an X-ray radiation source that provided monochromatized radiation at 14 keV using the CMMI system 100 as shown in FIG. 1A. The coded mask 105 was a binary mask with a pixel size of 5 μm, as shown in FIG. 3B. The distance from the mask 105 to the sample 110 was set to 53 mm, and the distance from the sample 110 to the detector 108 was set to 640 mm. FIG. 9A is an X-ray image of horizontal differential phase, FIG. 9B is an image of vertical differential phase, FIG. 9C is an image of phase reconstruction, FIG. 9D is a transmission image, and FIG. 9E is a scattering (i.e., dark-field) image of the elytra. The images of FIGS. 9A-9E demonstrate the ability of the CMMI system 100 to image different parts and features of the elytra by utilizing different phase reconstruction methods using a single captured image.

The following list of aspects reflects a variety of the embodiments explicitly contemplated by the present disclosure. Those of ordinary skill in the art will readily appreciate that the aspects below are neither limiting of the embodiments disclosed herein, nor exhaustive of all of the embodiments conceivable from the disclosure above, but are instead meant to be exemplary in nature.

1. An imaging system comprising: a radiation source disposed along an optical axis, the radiation source configured to generate radiation that propagates along the optical axis, and wherein the radiation has an intensity profile and a phase profile; a coded mask disposed along the optical axis such that the radiation impinges upon the coded mask, the coded mask configured to alter the phase and intensity profiles of the radiation according to a pre-determined phase and absorption mapping of the coded mask; and a detector system disposed along the optical axis configured to receive the radiation from the coded mask, and further configured to generate an electrical signal indicative of the received radiation.

2. An imaging system according to aspect 1, wherein the radiation comprises X-ray radiation.

3. An imaging system according to either aspect 1 or aspect 2, wherein the radiation source comprises (i) an undulator, (ii) a wiggler, (iii) a synchrotron, (iv) a free electron laser (FEL), or a laboratory X-ray source.

4. An imaging system according to any of aspects 1 to 3, wherein the intensity and phase profiles of the radiation comprise predetermined intensity and phase profiles.

5. An imaging system according to any of aspects 1 to 4, wherein the intensity and phase profiles of the radiation comprise predetermined intensity and phase profiles.

6. An imaging system according to any of aspects 1 to 5, wherein the coded mask comprises a binary coded absorption, phase, or absorption/phase mask.

7. An imaging system according to any of aspects 1 to 5, wherein the coded mask comprises a multi-level coded, a continuous coded, or a random coded, or a pseudo-random coded phase and/or absorption/phase mask.

8. An imaging system according to any of aspects 1 to 7, wherein the coded mask comprises a plurality of pixels including one or more phase pixels, absorption pixels, or phase and absorption pixels.

9. An imaging system according to aspect 8, wherein the plurality of pixels comprises pixels having transverse spatial dimensions of 0.1 to 50 micrometers.

10. An imaging system according to either aspect 8 or 9, wherein the plurality of pixels comprises a two-dimensional array of pixels.

11. An imaging system according to aspect 10, wherein the two-dimensional array of pixels comprises a 500 pixel by 500 pixel two-dimensional array of pixels.

12. An imaging system according to any of aspects 1 to 11, wherein the coded mask is configured to alter the phase profile of the radiation according to a multilevel phase mapping of the coded mask.

13. An imaging system according to any of aspects 1 to 11, wherein the coded mask is further configured to alter the intensity profile of the radiation.

14. An imaging system according to any of aspects 1 to 13, wherein the coded mask comprises a material selected from the group consisting of gold, nickel, copper, silicon, bismuth platinum, diamond, a polymer, and other materials to create sufficient intensity contrast (>1%) on the detector for the CMMI reconstruction.

15. An imaging system according to any of aspects 1 to 14, wherein the coded mask has a thickness along the optical axis to produce sufficient intensity contrast (>1%) on the detector for the CMMI reconstruction.

16. An imaging system according to any of aspects 1 to 15, further comprising a processor configured to execute computer-executable instructions stored on one or more tangible-non-transitory memories to: obtain the electrical signal indicative of the received radiation; determine from the obtained electrical signal a light field image; and determine from the obtained electrical signal a dark field image.

17. An imaging system according to aspect 16, wherein to determine the light field image, the computer-executable instructions further cause the processor to perform a minimization procedure.

18. An imaging system according to either aspect 16 or 17, wherein to determine the light field image, the computer-executable instructions further cause the processor to perform a machine learning method.

19. An imaging system according to any of aspects 1 to 18, wherein the coded mask comprises an aperture or a plate.

A. A method of imaging a sample, the method comprising: providing, by a radiation source, radiation to a coded mask, the radiation propagating along an optical axis and the radiation having an intensity profile and a phase profile; altering, by the coded mask disposed along the optical axis, the phase and intensity profile of the radiation according to a pre-determined phase and absorption mapping of the coded mask; and detecting, by a detector system disposed along the optical axis, the radiation, the detector configured to generate an electrical signal indicative of the received radiation.

A+1. A method according to aspect A, wherein the radiation comprises X-ray radiation.

A+2. A method according to either aspect A or A+1, wherein the radiation source comprises (i) an undulator, (ii) a wiggler, (iii) a synchrotron, (iv) a free electron laser (FEL), or a laboratory X-ray source.

A+3. A method according to any of aspects A to A+2, wherein the intensity and phase profiles of the radiation comprise plane wave intensity and phase profiles.

A+4. A method according to any of aspects A to A+3, wherein the intensity and phase profiles of the radiation comprise predetermined intensity and phase profiles.

A+5. A method according to any of aspects A to A+4, wherein the coded mask comprises a binary coded absorption, phase, and/or absorption and phase mask.

A+6. A method according to any of aspects A to A+4, wherein the coded mask comprises a multi-level coded, a continuous coded, or a random coded, or a pseudo-random coded phase and/or absorption and phase mask.

A+7. A method according to any of aspects A to A+6, wherein the coded mask comprises a plurality of pixels including one or more phase pixels, absorption pixels, or phase and absorption pixels.

A+8. A method according to aspect A+7, wherein the plurality of pixels comprises pixels having transverse spatial dimensions of 0.1 to 50 micrometers.

A+9. A method according to either aspect A+7 or A+8, wherein the plurality of pixels comprises a two-dimensional array of pixels.

A+10. A method according to aspect A+9, wherein the two-dimensional array of pixels comprises a 100 pixel by 100 pixel two-dimensional array of pixels.

A+11. A method according to any of aspects A to A+10, wherein the coded mask is configured to alter the phase profile of the radiation according to a multilevel phase mapping of the coded mask.

A+12. A method according to any of aspects A to A+11, wherein the coded mask is further configured to alter the intensity profile of the radiation.

A+13. A method according to any of aspects A to A+12, wherein the coded mask comprises a material selected from the group consisting of gold, nickel, copper, silicon, bismuth platinum, diamond, a polymer, and other materials to create sufficient intensity contrast (>1%) on the detector for the CMMI reconstruction.

A+14. A method according to any of aspects A to A+13, wherein the coded mask has a thickness along the optical axis of to produce sufficient intensity contrast (>1%) on the detector for the CMMI reconstruction.

A+15. A method according to any of aspects A to A+14, further comprising: obtaining, by a processor configured to execute computer-executable instructions stored on one or more tangible-non-transitory memories, the electrical signal indicative of the of the received radiation; determining, by the processor, a light field image from the obtained electrical signal; and determining, by the processor, a dark field image from the obtained electrical signal.

A+16. A method according to aspect A+15, wherein determining a light field image comprises performing a maximum-likelihood optimization.

A+17. A method according to either aspect A+15 or A+16, wherein determining a light field image comprises performing a machine learning method.

A+18. A method according to any of aspects A+15 to A+16, wherein the coded mask comprises an aperture or a plate.

What is claimed is:

1. An imaging system comprising:
    a radiation source disposed along an optical axis, the radiation source configured to generate radiation that propagates along the optical axis, and wherein the radiation has an intensity profile and a phase profile;
    a coded mask disposed along the optical axis such that the radiation impinges upon the coded mask, the coded mask configured to alter the phase profile of the radiation according to a pre-determined phase mapping of the coded mask, the pre-determined phase mapping being a speckle pattern; and
    a detector system disposed along the optical axis configured to receive the radiation from the coded mask, and further configured to generate an electrical signal indicative of the received radiation.

2. An imaging system according to claim 1, wherein the radiation comprises X-ray radiation.

3. An imaging system according to claim 1, wherein the intensity profile and the phase profile of the radiation comprise, respectively, a predetermined intensity profile and a predetermined phase profile.

4. An imaging system according to claim 1, wherein the coded mask comprises a binary coded mask.

5. An imaging system according to claim 1, wherein the coded mask comprises a plurality of pixels.

6. An imaging system according to claim 5, wherein the plurality of pixels comprises pixels having transverse spatial dimensions of 0.1 to 50 micrometers.

7. An imaging system according to claim 1, wherein the coded mask is configured to alter the phase profile of the radiation according to a multilevel phase mapping of the coded mask.

8. An imaging system according to claim 1, further comprising:
    one or more tangible-non-transitory memories; and
    a processor configured to execute computer-executable instructions stored on the one or more tangible-non-transitory memories to:
        obtain the electrical signal indicative of the received radiation;
        determine from the obtained electrical signal a light field image; and
        determine from the obtained electrical signal a dark field image.

9. An imaging system according to claim 8, wherein to determine the light field image, the computer-executable instructions further cause the processor to perform a maximum-likelihood optimization.

10. An imaging system according to claim 8, wherein to determine the light field image, the computer-executable instructions further cause the processor to perform a machine-learning method.

11. A method of imaging a sample, the method comprising:

providing, by a radiation source, radiation to a coded mask, the radiation propagating along an optical axis, and the radiation having an intensity profile and a phase profile;

altering, by the coded mask disposed along the optical axis, the phase profile of the radiation according to a pre-determined phase mapping of the coded mask, the pre-determined phase mapping being a speckle pattern; and receiving, by a detector system disposed along the optical axis, the radiation, the detector system configured to generate an electrical signal indicative of the received radiation.

12. A method according to claim 11, wherein the radiation comprises X-ray radiation.

13. A method according to claim 11, wherein the intensity profile and the phase profile of the radiation comprise, respectively, a predetermined intensity profile and a predetermined phase profile.

14. A method according to claim 11, wherein the coded mask comprises a binary coded mask.

15. A method according to claim 11, wherein the coded mask comprises a plurality of pixels.

16. A method according to claim 15, wherein the plurality of pixels comprises pixels having transverse spatial dimensions of 0.1 to 50 micrometers.

17. A method according to claim 11, wherein the coded mask is further configured to alter the intensity profile of the radiation.

18. A method according to claim 11, further comprising:
obtaining, by a processor configured to execute computer-executable instructions stored on one or more tangible-non-transitory memories, the electrical signal indicative of the received radiation;
determining, by the processor, a light field image from the obtained electrical signal; and
determining, by the processor, a dark field image from the obtained electrical signal.

19. A method according to claim 18, wherein determining the light field image comprises performing a maximum-likelihood optimization.

20. A method according to claim 18, wherein determining the light field image comprises performing a machine-learning method.

* * * * *